US012648895B2

(12) United States Patent
Zeng et al.

(10) Patent No.: US 12,648,895 B2
(45) Date of Patent: Jun. 9, 2026

(54) METHOD FOR PRODUCING COSMETIC SOLID POWDER

(71) Applicant: SHANGHAI ZHENCHUN COSMETICS CO., LTD., Shanghai (CN)

(72) Inventors: Sili Zeng, Shanghai (CN); Xiaohua Cui, Shanghai (CN); Lijuan Cheng, Shanghai (CN)

(73) Assignee: SHANGHAI ZHENCHUN COSMETICS CO., LTD., Shanghai (CN)

( * ) Notice: Subject to any disclaimer, the term of this patent is extended or adjusted under 35 U.S.C. 154(b) by 1072 days.

(21) Appl. No.: 17/604,768

(22) PCT Filed: Apr. 17, 2020

(86) PCT No.: PCT/CN2020/085277
§ 371 (c)(1),
(2) Date: Oct. 19, 2021

(87) PCT Pub. No.: WO2020/216138
PCT Pub. Date: Oct. 29, 2020

(65) Prior Publication Data
US 2022/0192932 A1 Jun. 23, 2022

(30) Foreign Application Priority Data

Apr. 22, 2019 (CN) .......................... 201910322033.0

(51) Int. Cl.
| | |
|---|---|
| *A61K 8/02* | (2006.01) |
| *A61K 8/31* | (2006.01) |
| *A61K 8/34* | (2006.01) |
| *A61K 8/73* | (2006.01) |
| *A61K 8/92* | (2006.01) |
| *A61Q 1/12* | (2006.01) |
| *A61Q 19/00* | (2006.01) |

(52) U.S. Cl.
CPC ................ *A61K 8/022* (2013.01); *A61K 8/31* (2013.01); *A61K 8/345* (2013.01); *A61K 8/731* (2013.01); *A61K 8/922* (2013.01); *A61Q 1/12* (2013.01); *A61Q 19/00* (2013.01)

(58) Field of Classification Search
CPC .......... A61K 8/022; A61K 8/31; A61K 8/345; A61K 8/731; A61K 8/922; A61K 2800/80; A61K 8/73; A61K 2800/10; A61K 2800/84; A61K 8/25; A61K 8/29; A61K 8/8152; A61K 8/88; A61K 2800/43; A61Q 1/12; A61Q 19/00
See application file for complete search history.

(56) References Cited

U.S. PATENT DOCUMENTS

| | | | | |
|---|---|---|---|---|
| 5,814,311 A | * | 9/1998 | Le Bras-Roulier | .......................... A61K 8/0254 514/844 |
| 5,958,389 A | * | 9/1999 | Le Bras-Roulier | ...... A61Q 1/12 424/59 |
| 2010/0272834 A1 | * | 10/2010 | Malessa | ................. A61K 8/733 264/28 |

FOREIGN PATENT DOCUMENTS

| | | |
|---|---|---|
| CN | 107260557 A | 10/2017 |
| CN | 107280979 A | 10/2017 |
| CN | 107802527 A | 3/2018 |
| EP | 2392311 † | 7/2011 |
| EP | 3369412 A1 | 9/2018 |
| JP | S6253914 † | 3/1987 |
| JP | H072621 B2 | 1/1995 |
| JP | H08208432 A | 8/1996 |
| JP | 2011251956 A | 12/2011 |
| JP | 2012211113 A | 11/2012 |
| JP | 201465691 A | 4/2014 |

OTHER PUBLICATIONS

International Search Report, issued in PCT/CN2020/085277, dated Jul. 21, 2020.
Written Opinion, issued in PCT/CN2020/085277, dated Jul. 21, 2020.
European search opinion, issued in European Application No. 20795208.6, dated Apr. 5, 2023.
European Search Report, issued in EP20795208, by European Patent Office, dated Apr. 5, 2023.
Examination Report, issued in P00202110328, by Ministry of Law and Human Rights Republic of Indonesia Directorate General of Intellectual Property, dated Mar. 10, 2023.
Examination Report, issued in P00202110328, by Ministry of Law and Human Rights Republic of Indonesia Directorate General of Intellectual Property, dated Mar. 26, 2025.
Examination Search Report, issued in Canadian Patent Application No. 3137387, dated Oct. 27, 2023.
Office Action, issued in 9-5-2024-015656993, by Korean Patent Office, dated Feb. 20, 2024.
Office Action, issued in 9-5-2024-095849502, by Korean Patent Office, dated Nov. 9, 2024.
Office Action, issued in 9-5-2025-070167116, by Korean Patent Office, dated Jul. 24, 2025.

(Continued)

*Primary Examiner* — Jeffrey T. Palenik
(74) *Attorney, Agent, or Firm* — Zhu Lehnhoff LLP

(57) ABSTRACT

A method for producing a solid powder includes the following steps: (1) mixing the powders to obtain a material A, in which the powders include a flaky filler, a spherical filler, and a pigment; and mixing a natural polysaccharide with water, then adding an emollient moisturizer and an emulsifier to obtain a material B; (2) mixing the material A and the material B, and then adding a preservative to obtain a dispersion; (3) filling the dispersion into a mold; (4) freezing the dispersion to a preset low temperature, and then demolding to obtain a semi-finished product; and (5) drying the semi-finished product to obtain a finished product in a lyophilizer.

20 Claims, 3 Drawing Sheets

(56)          References Cited

OTHER PUBLICATIONS

Office Action, issued in Thai Patent Application No. 2101006447,
by Thai Patent Office, dated Apr. 18, 2024.
Rejection Decision, issued in Japanese Patent Application No.
2021-563275, dated May 23, 2023.

\* cited by examiner
† cited by third party

| Demoulding temperature of sample | Demoulding 30 minutes after filling | Demoulding 4 hours after filling |
|---|---|---|
| 25℃ | 1A | 1B |
| 1℃ | 1C | 1D |
| -15℃ freezing | 1E | 1F |

FIG. 5

METHOD FOR PRODUCING COSMETIC SOLID POWDER

TECHNICAL FIELD

The present disclosure relates to a cosmetic production method, and in particular to a method for producing a cosmetic solid powder.

BACKGROUND

At present, the solid powders commonly got available in the market are mainly produced by a powder pressing process. The components in the material used in the powder pressing process include an inorganic filler, a pearlescent pigment, a metallic soap, an oil, a preservative and a skin conditioning agent. The powder pressing process includes uniformly mixing and dispersing the inorganic filler, the pearlescent pigment and other powder components with the oil component by mechanical stirring to obtain a powder mixture, then filling the mixture to a metal plate or a plastic plate, and molding by pressing filling by a metal mold to obtain a cosmetic as a solid powder. The powder pressing process has mainly two disadvantages. a. High requirements are raised for the selection of materials used in the formulation. Particularly, the proportion of low-density microspheres needs to be reduced, otherwise, the products obtained are prone to cracks, breakage, or looseness. However, low-density microspheres have good effect on the soft focus, oil control, and long-lasting effects of the formulation, and the mentioned makeup effects cannot be achieved if the amount is reduced. b. There are also disadvantages in the process. Dust particles exist in the environment are large, and the loss of powder is serious, so rough edge tends to occur, which is caused to fall off easily due to vibration or the like during transportation.

In order to overcome the drawbacks of the powder pressing process, a wet powder filling process is usually used. The wet powder process includes mixing an organic solvent with a powder, stirring until uniform to form a slurry, placing the slurry in a container, then pumping the slurry into a syringe through a transfer pump, next injecting the slurry through the nozzle of the syringe into a plastic box via a filling port at the bottom of the container box, sealing the container box by pressing down a block, evacuating the volatile solvent while pressing down, and finally baking the container box in an environment at 40-60° C. However, the wet powder process also has the following defects. a. The commonly used solvents, for example, isomeric dodecane and isopropanol, are harmful to the environment and the human body during the volatilization process. b. It is difficult to guarantee that these trace solvents are not contained in the resulting products.

Moreover, both the dry and wet pressing processes are limited in complicated shape. Patterning on the solid powder is achieved under pressure. If the shape is complicated, it is difficult to attain a uniform pressure, so that the solid powder includes a brittle or breakable region. In addition, the formation of a three-dimensional pattern on the surface of the solid powder requires the engraving of the pattern on a metal mold. To prevent the material from being caught in the engraved pattern on the metal mold, a planar insulation cloth needs to be disposed between the metal mold and the material to be pressed. The planar insulation cloth is required to have a certain thickness, and an elastic tension inevitably exists during the pressing down process. If the pattern on the metal mold is too fine, a clear pattern cannot be formed on the surface due to the elastic tension and the thickness of the planar insulation cloth.

SUMMARY

Accordingly, the present disclosure is to provide a method for producing a cosmetic solid powder.

The present disclosure provides a method for producing a solid powder. The method includes the following steps: (1) mixing a powder phase uniformly to obtain a material A; and mixing a natural polysaccharide with a suitable amount of water uniformly, then adding an emollient moisturizer and an emulsifier, and then mixing uniformly, to obtain a material B, in which the powder phase includes a flaky filler, a spherical filler, and a pigment; (2) mixing the material A and the material B uniformly, and then adding a preservative to obtain a dispersion; (3) filling the dispersion into a mold; (4) freezing the dispersion to a preset low temperature, and then demolding to obtain a semi-finished product; and (5) drying the semi-finished product to obtain a finished product.

In the step (1), the natural polysaccharide and water are mixed at a temperature between 5° and 95° C.

In the step (3), the dispersion may be filled into a mold by injecting the dispersion at room temperature under a pressure between 0.2 bars and 1 bars or the dispersion may be heated to a preset high temperature, and then filed into a mold. The preset high temperature may be 50 to 95° C.

In the step (4), the pre-set low temperature is 5 to −20° C. In an embodiment, the pre-set low temperature is 0° C. to −20° C. The use of low temperature and in particular the use of freezing before demoulding enables to obtain a smooth and complete without any damage.

In the method of the disclosure, the demoulding is carried out before the drying step, which facilitates the implementation of the method.

In the step (5), the percentage by weight of water in the finished product is 5 or less.

In the step (5), lyophilization is adopted, which includes: placing the semi-finished product in a lyophilizer, and continuously freezing at a low temperature, where the temperature in the lyophilizer is lower than the eutectic point; then evacuating, and sublimation drying by properly heating after the vacuum level reaches a preset vacuum value, to remove the ice crystal; and finally desorption drying after sublimation, to remove the bound water. Contrary to the heat drying, the freeze drying does not cause shrinkage or adhesion of the product to the mold.

In one embodiment, the method for producing a solid powder, includes the following steps: (1) mixing a powder phase uniformly to obtain a material A; and mixing a natural polysaccharide with a suitable amount of water uniformly, then adding an emollient moisturizer and an emulsifier, and then mixing uniformly, to obtain a material B, wherein the powder phase includes a flaky filler, a spherical filler, and a pigment; (2) mixing the material A and the material B uniformly, and then adding a preservative to obtain a dispersion; (3) heating the dispersion to a preset high temperature, and then filling into a mold; (4) freezing the dispersion to a preset low temperature, and then demolding to obtain a semi-finished product; and (5) drying the semi-finished product to obtain a finished product wherein, lyophilization is adopted, which includes: placing the semi-finished product in a lyophilizer, and continuously freezing at a low temperature, wherein the temperature in the lyophilizer is lower than the eutectic point; then evacuating, and sublimation drying by properly heating after the vacuum level reaches a preset vacuum value, to remove the ice crystal; and finally desorption drying after sublimation, to remove the bound water.

In another embodiment, the method for producing a solid powder, includes the following steps: (1) mixing a powder phase uniformly to obtain a material A; and mixing a natural polysaccharide with a suitable amount of water uniformly, then adding an emollient moisturizer and an emulsifier, and then mixing uniformly, to obtain a material B, wherein the powder phase includes a flaky filler, a spherical filler, and a pigment; (2) mixing the material A and the material B uniformly, and then adding a preservative to obtain a dispersion; (3) filling into a mold the dispersion by injecting it at room temperature under a pressure between 0.2 bars and 1 bars; (4) freezing the dispersion to a preset low temperature, and then demolding to obtain a semi-finished product; and (5) drying the semi-finished product to obtain a finished product, in which lyophilization is adopted, which includes: placing the semi-finished product in a lyophilizer, and continuously freezing at a low temperature, in which the temperature in the lyophilizer is lower than the eutectic point; then evacuating, and sublimation drying by properly heating after the vacuum level reaches a preset vacuum value, to remove the ice crystal; and finally desorption drying after sublimation, to remove the bound water.

Further, the temperature in the lyophilizer is −10 to −60° C., the preset vacuum value is 10-70 Pa, the desorption drying temperature is 5 to 70° C., and the pressure is 10 to 70 Pa.

The content in parts by weight of the powder phase is 30 to 60, the content in parts by weight of the natural polysaccharide is 0.1 to 5, the content in parts by weight of the emollient moisturizer is 0.5 to 20, the content in parts by weight of the emulsifier is 0 to 5, and the content in parts by weight of the preservative is 0.05 to 3.

In an embodiment, the content in parts by weight of the natural polysaccharide is between 0.1 and 0.15.

The flaky filler is a mixture of talc, mica, kaolin, lauroyl lysine, boron nitride or any combination thereof. The spherical filler is a mixture of PMMA, nylon-12, polyurethane or HDI/trimethylolhexyllactonecrosspolymer, silica or any combination thereof. The pigment is a mixture of an inorganic pigment, an organic pigment, a pearlescent pigment or any combination thereof, in which the inorganic pigment includes titania, iron oxide red, yellow, and black, manganese violet, ultramarine blue, optionally hydrated chromium oxide, and iron blue; the organic pigments include cochineal red, red 6, red 7, blue 1, yellow 5, and red 28 lake pigments. The pearlescent pigment includes white pearlescent pigment, colored or dyed pearlescent pigments, organic or inorganic pigment-containing mica, glass, and synthetic fluorophlogopite-based dyed pearlescent pigments, and metal oxide pearlescent pigments. The natural polysaccharide is a mixture of cellulose and its derivatives, xanthan gum, Chondruscrispus, agar, gum arabic, starch and its derivatives, Curdlan, gelatin, gellan gum, konjac glucomannan, mannitol, xylan or any combination thereof. Preferably, the natural polysaccharide is xanthan gum. The emollient moisturizer is a fat, a polyol or a combination thereof, where the oil includes oil or wax of plant, mineral, animal or synthetic origin, grape seed oil, Meadowfoam seed oil, hydrogenated vegetable oil, avocado oil, Shea butter, white oil, cetearylethylhexanoate, squalane, octyldodecylstearoyl stearate, propylene carbonate, isodecyl pivalate, polydimethylsiloxane, beeswax, and white wax. The polyol includes glycerin, butanediol, propylene glycol, and dipropylene glycol. The emulsifier is a mixture of PEG-26-PPG-30 phosphate, Tween-20, Tween-80, Tween-60, alkyl polyglycoside, polyoxyethyleneoleate, polyoxyethylene laurate, glyceryl stearate citrate or any combination thereof. The preservative is a mixture of chlorphenesin, methylparaben, phenoxyethanol, ethylhexyl glycerol, capryl glycol, or any combination thereof.

The content in parts by weight of mica is 20, the content in parts by weight of PMMA is 3, the content in parts by weight of nylon-12 is 3, the content in parts by weight of silica is 2, the content in parts by weight of titania is 5, the content in parts by weight of Chondruscrispus is 1, the content in parts by weight of xanthan gum is 1, the content in parts by weight of mannitol is 3, the content in parts by weight of glycerin is 0.5, the content in parts by weight of ethylhexyl glycerol is 2.5, and the content in parts by weight of capryl glycol is 0.5.

In a first alternative embodiment, the content in parts by weight of mica is 8, the content in parts by weight of PMMA is 3, the content in parts by weight of silica is 2, the content in parts by weight of the pearlescent pigment is 30, the content in parts by weight of Chondruscrispus is 0.1, the content in parts by weight of glycerin is 2, the content in parts by weight of squalane is 1, the content in parts by weight of hydrogenated vegetable oil is 2, the content in parts by weight of Tween-80 is 1, and the content in parts by weight of methylparaben is 0.05.

In a second alternative embodiment, the content in parts by weight of mica is 10, the content in parts by weight of PMMA is 3, the content in parts by weight of the pearlescent pigment is 30, the content in parts by weight of *Chondrus crispus* is 0.3, the content in parts by weight of xanthan gum is 0.15, the content in parts by weight of glycerin is 2, the content in parts by weight of squalane is 5, the content in parts by weight of hydrogenated vegetable oil is 2, the content in parts by weight of Tween-80 is 1, the content in parts by weight of PEG-26-PPG-30 phosphate is 0.5, the content in parts by weight of methylparaben is 0.05, and the content in parts by weight of ethylhexyl glycerol is 1.

In a third alternative embodiment, the content in parts by weight of mica is 10, the content in parts by weight of silica is 2, the content in parts by weight of the pearlescent pigment is 48, the content in parts by weight of Chondruscrispus is 0.3, the content in parts by weight of xanthan gum is 0.15, the content in parts by weight of glycerin is 2, the content in parts by weight of Tween-80 is 1, the content in parts by weight of PEG-26-PPG-30 phosphate is 1, the content in parts by weight of methylparaben is 0.05, and the content in parts by weight of chlorphenesin is 0.1.

The mold is made of TPR, TPE, silicone rubber or rubber, In an embodiment, the mold is made of silicone rubber or rubber.

The method for producing a solid powder according to the present disclosure improves the cohesion by virtue of the natural polysaccharide and the emollient moisturizer, so that the demoulding is convenient, the surface of the finished product is three-dimensional, smooth, and easy to be made into various three-dimensional shapes, and once demolded, the subsequent operations can all be done with no need of the mold and the steps are simple and easy to operate.

The concept, the specific structure and the technical effects produced by the present disclosure will be further described for better understanding of the objects, features and effects of the present disclosure.

BRIEF DESCRIPTION OF THE DRAWINGS

To more clearly explain the technical solutions in the embodiments of the present disclosure, the drawings used in the description of the embodiments will be briefly described below. The drawings in the following description are merely exemplary embodiments of the present disclosure. For those of ordinary skill in the art, other drawings may also be obtained based on these drawings without any creative work.

FIG. 5 shows the effect of the demoulding temperature.

DETAILED DESCRIPTION

Figure 1:
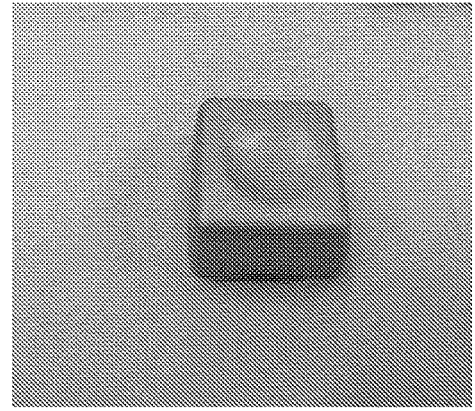
FIG. 1 shows a picture of a qualified sample.

The disclosure will now be described in detail with reference to the accompanying drawings and examples. As will be apparent to one skilled in the art, the embodiments described in the present disclosure are merely exemplary and represent only a subset of all such embodiments. In particular, all other embodiments obtained by a person of ordinary skill in the art based on the embodiments of the present invention without creative efforts fall within the scope of the present disclosure.

The method for preparing a solid powder according to the present disclosure includes the following steps.

a. A powder phase is mixed uniformly to obtain a material A; and then a natural polysaccharide is mixed with a suitable amount of water, and then an emollient moisturizer and an emulsifier are added and mixed uniformly to obtain a material B, where the powder phase includes a flaky filler, a spherical filler, and a pigment, and the natural polysaccharide and water are mixed at a temperature between 50 to 95° C. for fully mixing.

b. The material A and the material B are mixed, and then a preservative is added to obtain a dispersion.

c. The dispersion is heated to a preset high temperature to have good fluidity, and then filled into a mold, where the preset high temperature is 50 to 95° C., the mold is made of a flexible material such as TPR, TPE, silicon rubber or rubber. In an embodiment, the mold is made of silicon rubber or rubber.

The dispersion is first frozen to a preset low temperature, and then demolded to obtain a semi-finished product, where the preset low temperature is 5 to –20° C. In an embodiment, the preset low temperature is 0° C. to –20° C.

e. The semi-finished product is dried to obtain a finished product, that is, a solid powder, where the percentages by weight of water in the finished product are 5 or less.

In the step e, lyophilization is adopted. The semi-finished product is placed in a lyophilizer, and continuously frozen at a low temperature, where the temperature in the lyophilizer is –10 to –60° C. Then the semi-finished product is evacuated, and subjected to sublimation drying by properly heating (at a temperature that is not higher than the eutectic point) after the vacuum level reaches a preset vacuum value, to remove the ice crystal, where the preset vacuum value is 10-70 Pa. Finally, the semi-finished product is subjected to desorption drying after sublimation, to remove the bound water, where the desorption drying temperature is 5 to 70° C. and the pressure is 10-70 Pa.

The flaky filler is a mixture of talc, mica, kaolin, lauroyl lysine, boron nitride or any combination thereof.

The spherical filler is a mixture of PMMA, nylon-12, polyurethane or HDI/trimethylolhexyllactonecrosspolymer, silica or any combination thereof.

The pigment is a mixture of an inorganic pigment, an organic pigment, a pearlescent pigment or any combination thereof, in which the inorganic pigment includes titania, iron oxide red, iron oxide yellow, and iron oxide black, manganese violet, ultramarine blue, optionally hydrated chromium oxide, and iron blue; and the organic pigments include cochineal red, red 6 lake pigment, red 7 lake pigment, blue 1 lake pigment, yellow 5 lake pigment, and red 28 lake pigment; the pearlescent pigment includes white pearlescent pigment, colored or dyed pearlescent pigments, organic or inorganic pigment-containing mica, organic or inorganic pigment-containing glass, organic or inorganic pigment-containing synthetic fluorophlogopite-based dyed pearlescent pigments, and metal oxide pearlescent pigments.

The natural polysaccharide is a mixture of cellulose and its derivatives, xanthan gum, Chondruscrispus, agar, gum arabic, starch and its derivatives, Curdlan, gelatin, gellan gum, konjac glucomannan, mannitol, xylan or any combination thereof.

The emollient moisturizer is a fat, a polyol or a combination thereof, where the oil includes oil or wax of plant, mineral, animal or synthetic origin, grape seed oil, Meadowfoam seed oil, hydrogenated vegetable oil, avocado oil, Shea butter, white oil, cetearylethylhexanoate, squalane, octyldodecylstearoyl stearate, propylene carbonate, isodecylpivalate, polydimethylsiloxane, beeswax, and white wax; the polyol includes glycerin, butanediol, propylene glycol, and dipropylene glycol.

The emulsifier is a mixture of PEG-26-PPG-30 phosphate, Tween-20, Tween-80, Tween-60, alkyl polyglycoside, polyoxyethyleneoleate, polyoxyethylene laurate, glyceryl stearate citrate or any combination thereof.

The preservative is a mixture of chlorphenesin, methylparaben, phenoxyethanol, ethylhexyl glycerol, capryl glycol, or any combination thereof.

In the production method, the parts by weight of the components are: the powder phase 30 to 60, the natural polysaccharide 0.1 to 5, the emollient moisturizer 0.5 to 20, the emulsifier 0 to 5, and the preservative 0.05 to 3.

The disclosure will be further illustrated by the following figure and example. However, the example and figure should not be interpreted in any way as limiting the scope of the present disclosure. Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated.

Example 1

TABLE 1

The composition of the solid powder in Example 1

| Component | Parts by weight | Category |
|---|---|---|
| Mica | 20 | Powder phase |
| PMMA | 3 | Powder phase |
| Nylon-12 | 3 | Powder phase |
| Silica | 2 | Powder phase |
| Titania | 5 | Powder phase |
| Chondruscrispus | 1 | Natural polysaccharide |
| Xanthan gum | 1 | Natural polysaccharide |
| Mannitol | 3 | Natural polysaccharide |
| Glycerol | 0.5 | Emollient moisturizer |
| Ethylhexyl glycerol | 2.5 | Preservative |
| Capryl glycol | 0.5 | Preservative |

The solid powder produced with these components has a pleasant touch feeling and is not amenable to deformation and surface defects.

Example 2

TABLE 2

The composition of the solid powder in Example 2

| Component | Parts by weight | Category |
|---|---|---|
| Mica | 8 | Powder phase |
| PMMA | 3 | Powder phase |
| Silica | 2 | Powder phase |
| Pearlescent pigment | 30 | Powder phase |
| Chondruscrispus | 0.1 | Natural polysaccharide |
| Glycerol | 2 | Emollient moisturizer |
| Squalane | 1 | Emollient moisturizer |
| Hydrogenated vegetable oil | 2 | Emollient moisturizer |
| Tween-80 | 1 | Emulsifier |
| Methylparaben | 0.05 | Preservative |

The solid powder produced with these components has a pleasant touch feeling, is not amenable to deformation and surface defects, and can be easily applied.

Example 3

TABLE 3

The composition of the solid powder in Example 3

| Component | Parts by weight | Category |
|---|---|---|
| PMMA | 3 | Powder phase |
| Silica | 2 | Powder phase |
| Pearlescent pigment | 25 | Powder phase |
| Chondruscrispus | 0.3 | Natural polysaccharide |
| Xanthan gum | 0.15 | Natural polysaccharide |
| Glycerol | 8 | Emollient moisturizer |
| Squalane | 10 | Emollient moisturizer |
| Hydrogenated vegetable oil | 2 | Emollient moisturizer |
| Tween-80 | 2 | Emulsifier |
| PEG-26-PPG-30 phosphate | 3 | Emulsifier |
| Methylparaben | 0.05 | Preservative |
| Ethylhexyl glycerol | 1 | Preservative |

The solid powder produced with these components has no problem in molding, but is relatively prone to deformation, has a slippery feeling, and cannot be easily taken by a brush. The emollient moisturizer is present in a content in percentages by weight of 20, and has an impact on the sample, so the upper limit of the content in percentages by weight of the emollient moisturizer is not exceed 20.

Example 4

The influence of different parameters of the method for producing a cosmetic solid powder have been assayed with the below composition.

Table 4-1. The composition of the solid powder in Example 4 Component Parts by weight Category

TABLE 4-1

The composition of the solid powder in Example 4

| Component | Parts by weight | Category |
|---|---|---|
| Mica | 10 | Powder phase |
| PMMA | 3 | Powder phase |
| Pearlescent pigment | 30 | Powder phase |
| Chondruscrispus | 0.3 | Natural polysaccharide |
| Xanthan gum | 0.15 | Natural polysaccharide |
| Glycerol | 2 | Emollient moisturizer |
| Squalane | 5 | Emollient moisturizer |
| Hydrogenated vegetable oil | 2 | Emollient moisturizer |
| Tween-80 | 1 | Emulsifier |
| PEG-26-PPG-30 phosphate | 0.5 | Emulsifier |
| Methylparaben | 0.05 | Preservative |
| Ethylhexyl glycerol | 1 | Preservative |

Effect of the Demoulding Temperature

The same content is filled into the same mold model, and the effect of cooling demoulding and freezing demoulding on the sample is observed. It is found that the effect of freezing demoulding is the better, and the surface of all samples is smooth and complete without damage. However, the surface of the cooling demoulded samples is damaged or the samples are not formed, so the preliminary conclusion is that the product can not be cooled demoulded, which proves that the effect of freezing demoulding is obviously better than that of cooling demoulding (see FIG. 5).

Effect of the Drying Conditions

The influence of different drying conditions on the sample was compared: three different drying methods were used: room temperature, 55° C. oven and freeze-drying. Because the surface of cooling demoulding samples is damaged, the method of demoulding after drying the samples in the oven at room temperature and 55° C. is adopted, while the method of freezing demoulding is adopted in the freeze-drying, and then the samples are freeze-dried, and the sample state is obtained by comparing different drying conditions:

More than 80% of the samples dried at room temperature can not be demoulded. The main reason for these samples that can not be demoulded is that the samples adhere to the mold, resulting in the destruction of the sample surface. The obvious shrinkage proportion of the samples accounts for more than 60%, and the good yield of the samples is 0.

For the samples dried at 55° C., more than 55% of the samples can not be demoulded. The main reason for these samples that can not be demoulded is that the samples adhere to the mold, resulting in the destruction of the sample surface; the proportion of the samples with obvious shrinkage is more than 60%, and the yield of the samples is less than 40%.

For the vacuum freeze-dried sample, the surface of the sample is complete without obvious shrinkage, and the good rate of the sample accounts for more than 85%, only the surface of the very other sample is slightly rough, and the good rate of the general sample accounts for more than 95%. See Table 4-1 below for details:

TABLE 4-2

Figure 2:
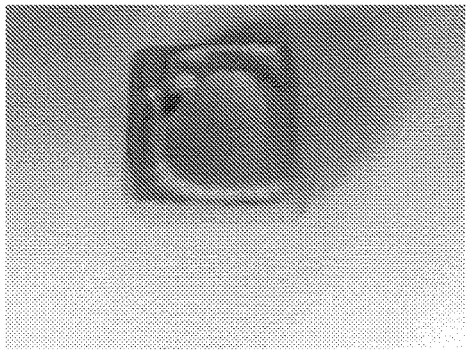
FIG. 2 shows a picture of sample with demouldingdommage.
Figure 3:
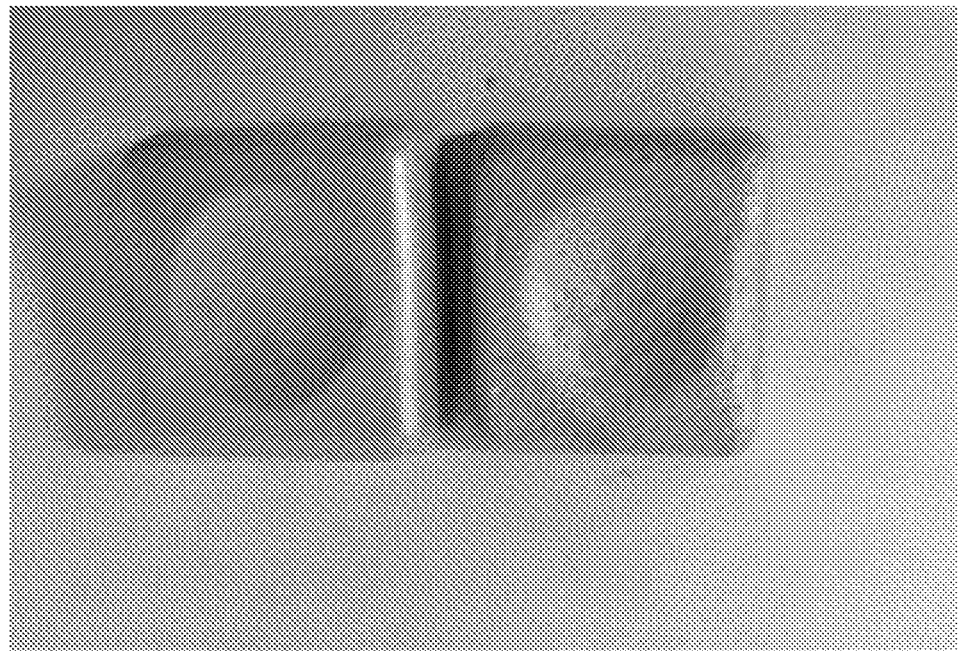
FIG. 3 shows a picture in which a sample with shrinkage is compared to a sample with non obvious shrinkage.
Figure 4:
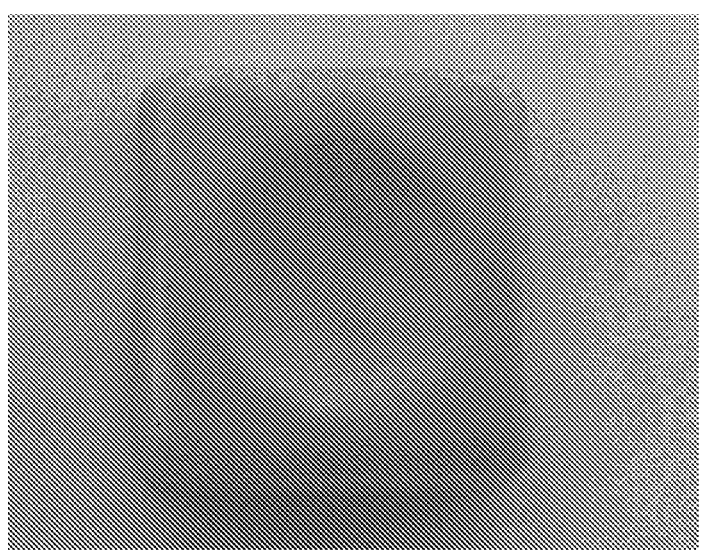
FIG. 4 shows a picture of sample with a slightly rough surface.

Illustrations of qualified samples, sample with demoulding damage, sample with shrinkage and sample with slightly rough surface are given in FIGS. 1-4.

| Factor | Can not be demolded | appearance is ok, not damaged | Description of sample shrinkage | qualification rate |
|---|---|---|---|---|
| freeze drying | 0 (Freeze demoulding ) | 95% qualified | not shrinkage | >85% |
| room temperature | 80% ( Dry demoulding ) | 100% Unqualified | 60% shrinkage | 0 |
| 55° C. dry | 55% ( Dry demoulding ) | 55% damaged | 60% shrinkage | <40% |

Example 5

TABLE 5

The composition of the solid powder in Example 5

| Component | Parts by weight | Category |
|---|---|---|
| Mica | 10 | Powder phase |
| Silica | 2 | Powder phase |
| Pearlescent pigment | 48 | Powder phase |
| Chondruscrispus | 0.3 | Natural polysaccharide |
| Xanthan gum | 0.15 | Natural polysaccharide |
| Glycerol | 2 | Emollient moisturizer |
| Tween-80 | 1 | Emulsifier |
| PEG-26-PPG-30 phosphate | 1 | Emulsifier |
| Methylparaben | 0.05 | Preservative |
| Chlorphenesin | 0.1 | Preservative |

The solid powder produced with these components is unlikely to deform or have surface defects, and can be easily picked up by finger or a brush for application.

Some embodiments of the present disclosure have been described in detail above. It will be appreciated that many modifications and variations can be made by those of ordinary skill in the art based on the concept of the present disclosure without creative efforts. Therefore, any technical solutions that can be obtained by a person skilled in the art according to the concept of the present disclosure based on the prior art by logic analysis, reasoning or limited experimentation are within the protection scope as defined by the claims.

What is claimed is:

1. A method for producing a solid powder, comprising the following steps: (1) mixing a powder phase uniformly to obtain a material A; and mixing a natural polysaccharide with a suitable amount of water uniformly, then adding an emollient moisturizer and an emulsifier, and then mixing uniformly, to obtain a material B, wherein the powder phase comprises a flaky filler, a spherical filler, and a pigment; (2) mixing the material A and the material B uniformly, and then adding a preservative to obtain a dispersion; (3) filling the dispersion into a mold; (4) freezing the dispersion to a preset low temperature, and then demolding to obtain a semi-finished product; and (5) drying the semi-finished product to obtain a finished product wherein lyophilization is adopted, which comprises: placing the semi-finished product in a lyophilizer, and continuously freezing at a low temperature, wherein the temperature in the lyophilizer is lower than the eutectic point; then evacuating, and sublimation drying by properly heating after the vacuum level reaches a preset vacuum value, to remove the ice crystal; and finally desorption drying after sublimation, to remove the bound water.

2. The method according to claim 1, wherein in the step (3): the dispersion is filled into a mold by injecting the dispersion at room temperature under a pressure between 0.2 bars and 1 bars; or the dispersion is heated to a preset high temperature and then filled into a mold.

3. The method according to claim 2, wherein in the step (1), the natural polysaccharide and water are mixed at a temperature between 50° C. and 95° C.; in the step (3), the preset high temperature is 50 to 95° C.; in the step (4), the pre-set low temperature is 5 to −20° C.; and in the step (5), the percentages by weight of water in the finished product is 5 or less.

4. The method according to claim 3, wherein the temperature in the lyophilizer is −10 to −60° C., the preset vacuum value is 10-70 Pa, the desorption drying temperature is 5 to 70° C., and the pressure is 10 to 70 Pa.

5. The method according to claim 4, wherein the content in parts by weight of the powder phase is 30 to 60, the content in parts by weight of the natural polysaccharide is 0.1 to 5, the content in parts by weight of the emollient moisturizer is 0.5 to 20, the content in parts by weight of the emulsifier is about 0 to 5, and the content in parts by weight of the preservative is 0.05 to 3.

6. The method according to claim 5, wherein the flaky filler is a mixture of talc, mica, kaolin, lauroyl lysine, boron nitride or any combination thereof, the spherical filler is a mixture of PMMA, nylon-12, polyurethane or HDI/trimethylol hexyllactone crosspolymer, silica or any combination thereof, the pigment is a mixture of an inorganic pigment, an organic pigment, a pearlescent pigment or any combination thereof, in which the inorganic pigment comprises titania, iron oxide red, iron oxide yellow, iron oxide black, manganese violet, ultramarine blue, optionally hydrated chromium oxide, and iron blue; and the organic pigments comprise cochineal red, red 6 lake pigment, red 7 lake pigment, blue 1 lake pigment, yellow 5 lake pigment, and red 28 lake pigment; the pearlescent pigment comprises white pearlescent pigment, colored or dyed pearlescent pigments, organic or inorganic pigment-containing mica, organic or inorganic pigment-containing glass, organic or inorganic pigment-containing synthetic fluorophlogopite-based dyed pearlescent pigments, and metal oxide pearlescent pigments; the natural polysaccharide is a mixture of cellulose and its derivatives, xanthan gum, *Chondrus crispus*, agar, gum arabic, starch and its derivatives, Curdlan, gelatin, gellan gum, konjac glucomannan, mannitol, xylan or any combination thereof, the emollient moisturizer is a fat, a polyol or a combination thereof, wherein the fat comprises oil or wax of plant, mineral, animal or synthetic origin, grape seed oil, Meadowfoam seed oil, hydrogenated vegetable oil, avocado oil, Shea butter, white oil, cetearyl ethylhexanoate, squalane, octyldodecyl stearoyl stearate, propylene carbonate, isodecyl pivalate, polydimethylsiloxane, beeswax, and white wax; the polyol comprises glycerin, butanediol, propylene glycol, and dipropylene glycol; the emulsifier is a mixture of PEG-26-PPG-30 phosphate, polysorbate-20, polysorbate-80, polysorbate-60, alkyl polyglycoside, polyoxyethylene oleate, polyoxyethylene laurate, glyceryl stearate citrate or any combination thereof, and the preservative is a mixture of chlorphenesin, methylparaben, phenoxyethanol, ethylhexyl glycerol, capryl glycol, or any combination thereof.

7. The method according to claim 6, wherein the content in parts by weight of mica is 20, the content in parts by weight of PMMA is 3, the content in parts by weight of nylon-12 is 3, the content in parts by weight of silica is 2, the content in parts by weight of titania is 5, the content in parts by weight of *Chondrus crispus* is 1, the content in parts by weight of xanthan gum is 1, the content in parts by weight of mannitol is 3, the content in parts by weight of glycerin is 0.5, the content in parts by weight of ethylhexyl glycerol is 2.5, and the content in parts by weight of capryl glycol is 0.5.

8. The method according to claim 6, wherein the content in parts by weight of mica is 8, the content in parts by weight of PMMA is 3, the content in parts by weight of silica is 2, the content in parts by weight of the pearlescent pigment is 30, the content in parts by weight of *Chondrus crispus* is 0.1, the content in parts by weight of glycerin is 2, the content in parts by weight of squalane is 1, the content in parts by weight of hydrogenated vegetable oil is 2, the content in parts by weight of polysorbate-80 is 1, and the content in parts by weight of methylparaben is 0.05.

9. The method according to claim 6, wherein the content in parts by weight of mica is 10, the content in parts by weight of PMMA is 3, the content in parts by weight of the pearlescent pigment is 30, the content in parts by weight of *Chondrus crispus* is 0.3, the content in parts by weight of xanthan gum is 0.15, the content in parts by weight of glycerin is 2, the content in parts by weight of squalane is 5, the content in parts by weight of hydrogenated vegetable oil is 2, the content in parts by weight of polysorbate-80 is 1, the content in parts by weight of PEG-26-PPG-30 phosphate is 0.5, the content in parts by weight of methylparaben is 0.05, and the content in parts by weight of ethylhexyl glycerol is 1.

10. The method according to claim 6, wherein the content in parts by weight of mica is 10, the content in parts by weight of silica is 2, the content in parts by weight of the pearlescent pigment is 48, the content in parts by weight of *Chondrus crispus* is 0.3, the content in parts by weight of xanthan gum is 0.15, the content in parts by weight of glycerin is 2, the content in parts by weight of polysorbate-80 is 1, the content in parts by weight of PEG-26-PPG-30 phosphate is 1, the content in parts by weight of methylparaben is 0.05, and the content in parts by weight of chlorphenesin is 0.1.

11. The method according to claim 5, wherein the mold is made of TPR, TPE, silicone rubber or rubber.

12. The method according to claim 1, wherein in the step (1), the natural polysaccharide and water are mixed at a temperature between 50° C. and 95° C.; in the step (3), the preset high temperature is 50 to 95° C.; in the step (4), the pre-set low temperature is 5 to −20° C.; and in the step (5), the percentages by weight of water in the finished product is 5 or less.

13. The method according to claim 1, wherein the temperature in the lyophilizer is −10 to −60° C., the preset vacuum value is 10-70 Pa, the desorption drying temperature is 5 to 70° C., and the pressure is 10 to 70 Pa.

14. The method according to claim 1, wherein the content in parts by weight of the powder phase is 30 to 60, the content in parts by weight of the natural polysaccharide is 0.1 to 5, the content in parts by weight of the emollient moisturizer is 0.5 to 20, the content in parts by weight of the emulsifier is about 0 to 5, and the content in parts by weight of the preservative is 0.05 to 3.

15. The method according to claim 14, wherein the mold is made of TPR, TPE, silicone rubber or rubber.

16. The method according to claim 1, wherein the flaky filler is a mixture of talc, mica, kaolin, lauroyl lysine, boron nitride or any combination thereof; the spherical filler is a mixture of PMMA, nylon-12, polyurethane or HDI/trimethylol hexyllactone crosspolymer, silica or any combination thereof; the pigment is a mixture of an inorganic pigment, an organic pigment, a pearlescent pigment or any combination thereof, in which the inorganic pigment comprises titania, iron oxide red, iron oxide yellow, iron oxide black, manganese violet, ultramarine blue, optionally hydrated chromium oxide, and iron blue; and the organic pigments comprise cochineal red, red 6 lake pigment, red 7 lake pigment, blue 1 lake pigment, yellow 5 lake pigment, and red 28 lake pigment; the pearlescent pigment comprises white pearlescent pigment, colored or dyed pearlescent pigments, organic or inorganic pigment-containing mica, organic or inorganic pigment-containing glass, organic or inorganic pigment-containing synthetic fluorophlogopite-based dyed pearlescent pigments, and metal oxide pearlescent pigments; the natural polysaccharide is a mixture of cellulose and its derivatives, xanthan gum, *Chondrus crispus*, agar, gum arabic, starch and its derivatives, Curdlan, gelatin, gellan gum, konjac glucomannan, mannitol, xylan or any combination thereof; the emollient moisturizer is a fat, a polyol or a combination thereof, wherein the fat comprises oil or wax of plant, mineral, animal or synthetic origin, grape seed oil, Meadowfoam seed oil, hydrogenated vegetable oil, avocado oil, Shea butter, white oil, cetearyl ethylhexanoate, squalane, octyldodecyl stearoyl stearate, propylene carbonate, isodecyl pivalate, polydimethylsiloxane, beeswax, and white wax; the polyol comprises glycerin, butanediol, propylene glycol, and dipropylene glycol; the emulsifier is a mixture of PEG-26-PPG-30 phosphate, polysorbate-20, polysorbate-80, polysorbate-60, alkyl polyglycoside, polyoxyethylene oleate, polyoxyethylene laurate, glyceryl stearate citrate or any combination thereof; and the preservative is a mixture of chlorphenesin, methylparaben, phenoxyethanol, ethylhexyl glycerol, capryl glycol, or any combination thereof.

17. The method according to claim 16, wherein the content in parts by weight of mica is 20, the content in parts by weight of PMMA is 3, the content in parts by weight of nylon-12 is 3, the content in parts by weight of silica is 2, the content in parts by weight of titania is 5, the content in parts by weight of *Chondrus crispus* is 1, the content in parts by weight of xanthan gum is 1, the content in parts by weight of mannitol is 3, the content in parts by weight of glycerin is 0.5, the content in parts by weight of ethylhexyl glycerol is 2.5, and the content in parts by weight of capryl glycol is 0.5.

18. The method according to claim 16, wherein the content in parts by weight of mica is 8, the content in parts by weight of PMMA is 3, the content in parts by weight of silica is 2, the content in parts by weight of the pearlescent pigment is 30, the content in parts by weight of *Chondrus crispus* is 0.1, the content in parts by weight of glycerin is 2, the content in parts by weight of squalane is 1, the content in parts by weight of hydrogenated vegetable oil is 2, the content in parts by weight of polysorbate-80 is 1, and the content in parts by weight of methylparaben is 0.05.

19. The method according to claim 16, wherein the content in parts by weight of mica is 10, the content in parts by weight of PMMA is 3, the content in parts by weight of the pearlescent pigment is 30, the content in parts by weight of *Chondrus crispus* is 0.3, the content in parts by weight of xanthan gum is 0.15, the content in parts by weight of glycerin is 2, the content in parts by weight of squalane is 5, the content in parts by weight of hydrogenated vegetable oil is 2, the content in parts by weight of polysorbate-80 is 1, the content in parts by weight of PEG-26-PPG-30 phosphate is 0.5, the content in parts by weight of methylparaben is 0.05, and the content in parts by weight of ethylhexyl glycerol is 1.

20. The method according to claim 16, wherein the content in parts by weight of mica is 10, the content in parts by weight of silica is 2, the content in parts by weight of the pearlescent pigment is 48, the content in parts by weight of *Chondrus crispus* is 0.3, the content in parts by weight of xanthan gum is 0.15, the content in parts by weight of glycerin is 2, the content in parts by weight of polysorbate-80 is 1, the content in parts by weight of PEG-26-PPG-30 phosphate is 1, the content in parts by weight of methylparaben is 0.05, and the content in parts by weight of chlorphenesin is 0.1.

* * * * *